United States Patent [19]

Ramachandran

[11] Patent Number: 4,536,343

[45] Date of Patent: Aug. 20, 1985

[54] PROCESS FOR PREPARING ALPHA-ARYLACRYLONITRILES

[75] Inventor: Venkataraman Ramachandran, Baton Rouge, La.

[73] Assignee: Ethyl Corporation, Richmond, Va.

[21] Appl. No.: 676,479

[22] Filed: Nov. 29, 1984

[51] Int. Cl.$^3$ .................. C07C 121/75; C07C 121/62; C07C 121/70

[52] U.S. Cl. ........................... 260/465 F; 260/465 G; 260/465 K

[58] Field of Search ............ 260/465 K, 465 G, 465 F

[56] References Cited

U.S. PATENT DOCUMENTS 4,132,728  1/1979  Verbrugge et al. ............ 260/465 G

OTHER PUBLICATIONS

Jacobs et al., J. Org. Chem., vol. 48, pp. 5134–5135, (1983).

*Primary Examiner*—Dolph H. Torrence
*Attorney, Agent, or Firm*—Donald L. Johnson; John F. Sieberth; Patricia J. Hogan

[57] ABSTRACT

An alpha-arylacrylonitrile is prepared by reacting an aryl ketone having a removable hydrogen alpha to the carbonyl group with an alkali metal cyanide and aluminum chloride, preferably in the presence of a solvent and a phase transfer catalyst. In a preferred embodiment, the aryl ketone is a tetralone, and the product is a 1-cyano-3,4-dihydronaphthalene which may then be dehydrogenated to a 1-cyanonaphthalene.

17 Claims, No Drawings

PROCESS FOR PREPARING ALPHA-ARYLACRYLONITRILES

FIELD OF INVENTION

This invention relates to alpha-arylacrylonitriles and more particularly to a process for preparing them.

BACKGROUND

It is known that alpha-arylacrylonitriles are useful as chemical intermediates and that they can be prepared in various ways. For example, Jacobs et al., *Journal of Organic Chemistry*, 1983, Vol. 48, pp. 5134–5135, teach that 6-methoxy-1-cyano-3,4-dihydronaphthalene is useful as an intermediate in the synthesis of steroids and that it can be prepared by (1) the addition of diethylaluminum cyanide to 6-methoxytetralone followed by dehydration or (2) the addition of cyanotrimethylsilane to 6-methoxytetralone followed by treatment with phosphoryl chloride in pyridine. As taught by Jacobs et al., the former method of synthesizing their alpha-arylacrylonitrile is impractical for large scale operations, and the latter method requires two steps.

SUMMARY OF INVENTION

An object of this invention is to provide a novel process for preparing alpha-arylacrylonitriles.

Another object is to provide such a process which is suitable for large scale operations and produces the alpha-arylacrylonitriles from aryl ketones in a single step.

These and other objects are attained by reacting an aryl ketone having a removable hydrogen alpha to the carbonyl group with an alkali metal cyanide and aluminum chloride.

DETAILED DESCRIPTION

Aryl ketones that can be used in the practice of the invention can be any aryl ketones having a removable hydrogen alpha to the carbonyl group. However, they are generally aryl ketones corresponding to the formula Ar—CO—R wherein Ar is aryl and R is a monovalent aliphatic, cycloaliphatic, or aromatic group having a removable hudrogen in the alpha-position. In such ketones the Ar group is generally an aryl group containing 1–20 carbons, most commonly a phenyl or naphthyl group which optionally bears one or more inert substituents, i.e., substituents that do not inhibit the activity of the aluminum chloride in removing the removable hydrogen, such as alkyl, alkylthio, alkoxy, halo, nitro, etc. The R group is generally a saturated or unsaturated aliphatic, cycloaliphatic, or aromatic group containing 1–20 carbons, optionally bearing one or more inert substituents and sometimes joined with the Ar group to form a fused ring.

Exemplary of such ketones are phenyl alkyl ketones wherein the alkyl group is methyl, ethyl, propyl, isopropyl, butyl, isobutyl, t-butyl, pentyl, hexyl, heptyl, octyl, nonyl, decyl, dodecyl, etc.; the corresponding substituted-phenyl alkyl ketones wherein the substituents on the benzene ring may be any of the aforementioned alkyl groups and/or the corresponding alkoxy or alkylthio groups, chloro, bromo, nitro, etc.; the corresponding naphthyl or substituted-naphthyl alkyl ketones; the corresponding aryl substituted-alkyl ketones wherein the substituents on the alkyl group may be any of the aforementioned inert substituents; the corresponding aryl substituted-or-unsubstituted-cycloalkyl (e.g., cyclopropyl, cyclobutyl, cyclohexyl, cyclooctyl, etc.) ketones; the corresponding aryl substituted-or-unsubstituted-alkenyl ketones wherein the unsaturation is at least one carbon removed from the carbon bearing the removable hydrogen, such as ketones in which the alkenyl group is 2-butenyl, 3-hexenyl, 4-hexenyl, 4-octenyl, etc.; the corresponding aryl substituted-or-unsubstituted-cycloalkenyl ketones; the corresponding aryl substituted-or-unsubstituted-aromatic ketones wherein said aromatic group is benzyl, phenylethyl, phenylpropyl, etc.; tetralone, etc. Among the preferred ketones are acetophenones, such as acetophenone, 4-chloroacetophenone, 4-isobutylacetophenone, 4-ethoxyacetophenone, etc., and tetralones, such as tetralone, 6-methoxytetralone, 7-bromotetralone, etc.

Alkali metal cyanides utilizable in the process are the lithium, sodium, potassium, rubidium, and cesium cyanides, with the sodium and potassium cyanides being preferred. To produce good yields of the desired product, it is generally desirable to employ about 1–5, preferably about 1–2, mols of alkali metal cyanide per mol of ketone.

The aluminum chloride employed in the process is used in the amount of about 1–1.5, preferably about 1–1.1, mols per mol of ketone.

Other ingredients that are suitably included in the reaction mixture are a solvent and a phase transfer catalyst. Solvents that may be employed include all solvents in which the reactants are soluble, such as aliphatic and aromatic hydrocarbons (e.g., toluene, xylenes, heptanes, etc.), chlorobenzene, nitrobenzene, etc. Particularly useful phase transfer catalysts are tetraalkylammonium halides, preferably bromides and halides, such as tetrabutylammonium bromide, tributylmethylammonium chloride, etc. When employed, the catalyst is used in a catalytic amount, e.g., about 2–6% by weight of the ketone; and its use permits the attainment of higher yields than can be obtained in its absence.

In the practice of the invention, the ingredients of the reaction mixture may be combined in any suitable manner and heated at a suitable temperature, e.g., about 60°–120° C., preferably about 90° C., to produce the desired product. The time required to obtain good yields varies with the temperature but is frequently in the range of about 4–10 hours. A preferred manner of combining the ingredients is to prestir the alkali metal cyanide, aluminum chloride, and a solvent until a reaction between the cyanide and aluminum chloride has been accomplished before combining these ingredients with the ketone.

The process is a cyanation/dehydration reaction which results in the formation of an alpha-arylacrylonitrile. When an aforementioned Ar—CO—R ketone is employed as the starting material, the product corresponds to the formula Ar—CCN=R', wherein Ar has the same meaning as given above and R' is the divalent group obtained by removing the removable hydrogen from R.

After completion of the reaction, the product can be recovered by conventional means or, alternatively, can be subjected to further reactions without being isolated when the further reactions would not be inhibited by impurities in the crude product. It is frequently desirable to subject the alpha-arylacrylonitrile to subsequent reactions. One such reaction is a dehydrogenation of a product such as 6-methoxy-1-cyano-3,4-dihydronaphthalene to a product such as 6-methoxy-1-cyanonaphthalene—a dehydrogenation that can be accomplished, e.g., by heating the reaction mixture, preferably at reflux temperatures, in the presence of a palladium-on-carbon catalyst or by other techniques known in the art.

The invention is particularly advantageous as a one-step, commercially-acceptable process for preparing alpha-arylacrylonitriles, especially 1-cyano-3,4-dihydronaphthalenes, that can then be converted to other products.

The following examples are given to illustrate the invention and are not intended as a limitation thereof.

EXAMPLE I

A mixture of 1.3 g of dry AlCl$_3$, 0.64 g of dry NaCN, and 87 ml of tetrabutylammonium bromide (TBAB) in 8.7 ml of dry nitrobenzene (NB) was stirred for two hours under a nitrogen atmosphere. Then 1.53 g of 6-methoxy-1-tetralone (6-MT) were added to provide a reaction mixture containing the 6-MT, NaCN, and AlCl$_3$ *I in a mol ratio of* 1/1.5/1.1 and containing 5.6% of TBAB, based on the weight of 6-MT. The reaction mixture was stirred at 90° C. for 10 hours to form 6-methoxy-1-cyano-3,4-dihydronaphthalene (6-MCDN). After workup the VPC ratio of 6-MT/6-MCDN was determined to be 8/92. The process resulted in an 85% isolated yield of 6-MCDN.

EXAMPLE II

Example I was essentially repeated except that the AlCl$_3$/NaCN/TBAB/NB mixture was not subjected to the two hour stirring period prior to the addition of the 6-MT. After workup the VPC ratio of 6-MT/6-MCDN was determined to be 41/59.

EXAMPLE III

Example I was essentially repeated except that the 6-MT was replaced with 4-methoxyphenyl 3-chloropropyl ketone and the amount of NaCN was reduced to only 1.3 molar proportions. VPC analysis showed a 70% conversion of the ketone to alpha-(4-methoxyphenyl)-beta-(2-chloroethyl)acrylonitrile.

EXAMPLE IV

A crude 6-MCDN in nitrobenzene prepared essentially as in Example I was treated with 5% (based on the weight of the original 6-MT) of 5% Pd/C at 150°–220° C. for 10 hours. The process resulted in the conversion of 97% of the 6-MCDN to 6-methoxy-1-cyanonaphthalene.

It is obvious that many variations can be made in the products and processes set forth above without departing from the spirit and scope of this invention.

I claim:

1. A process which comprises reacting an aryl ketone having a removable hydrogen alpha to the carbonyl group with an alkali metal cyanide and aluminum chloride so as to form an alpha-arylacrylonitrile.
2. The process of claim 1 wherein an aryl ketone corresponding to the formula Ar—CO—R is reacted with an alkali metal cyanide and aluminum chloride so as to form an alpha-arylacrylonitrile corresponding to the formula Ar—CCN=R', in which formulas Ar is aryl, R is a monovalent aliphatic, cycloaliphatic, or aromatic group having a removable hydrogen in the alpha-position, and R' is the divalent group obtained by removing the removable hydrogen from R.
3. The process of claim 2 wherein the aryl ketone is an acetophenone.
4. The process of claim 3 wherein the acetophenone is 4-isobutylacetophenone.
5. The process of claim 2 wherein the aryl ketone is a tetralone.
6. The process of claim 5 wherein the tetralone is 6-methoxytetralone.
7. The process of claim 1 wherein the alkali metal cyanide is sodium cyanide.
8. The process of claim 1 wherein the alkali metal cyanide is potassium cyanide.
9. The process of claim 1 wherein the reaction is conducted in a solvent.
10. The process of claim 9 wherein the solvent is nitrobenzene.
11. The process of claim 1 wherein the reaction is conducted in the presence of a catalytic amount of a phase transfer catalyst.
12. The process of claim 11 wherein the catalyst is a tetraalkylammonium halide.
13. The process of claim 12 wherein the tetraalkylammonium halide is tetrabutylammonium bromide.
14. The process of claim 1 wherein the reaction is conducted at a temperature of about 60°–120° C.
15. A process which comprises reacting a tetralone having a removable hydrogen alpha to the carbonyl group with an alkali metal cyanide and aluminum chloride in the presence of a catalytic amount of a tetraalkylammonium halide at a temperature of about 60°–120° C. so as to form a 1-cyano-3,4-dihydronaphthalene.
16. The process of claim 15 wherein the tetralone is 6-methoxy-1-tetralone and the product is 6-methoxy-1-cyano-3,4-dihydronaphthalene.
17. The process of claim 16 wherein the 6-methoxy-1-cyano-3,4-dihydronaphthalene is subsequently dehydrogenated to 6-methoxy-1-cyanonaphthalene.

* * * * *